United States Patent [19]

Rufer et al.

[11] 4,038,410
[45] July 26, 1977

[54] NITROIMIDAZOLE DERIVATIVES AND PROCESS FOR THE PREPARATION THEREOF

[75] Inventors: Clemens Rufer; Katica Schwarz; Hans-Joachim Kessler, all of Berlin, Germany

[73] Assignee: Schering Aktiengesellschaft, Berlin & Bergkamen, Germany

[21] Appl. No.: 557,539

[22] Filed: Mar. 12, 1975

[30] Foreign Application Priority Data

Mar. 14, 1974  Germany .............................. 2412656
Mar. 14, 1974  Germany .............................. 2412657

[51] Int. Cl.$^2$ ..................... A61K 9/22; C07D 239/22; C07D 403/04
[52] U.S. Cl. ............................ 424/273; 260/256.4 N; 260/256.4 R; 260/309; 260/309.6; 260/310 R; 260/307 H; 424/251
[58] Field of Search ................ 260/309.6, 309, 310 R; 424/273

[56] References Cited

U.S. PATENT DOCUMENTS 3,798,232  3/1974  Wittekind et al. ................ 260/309.6
3,883,549  5/1975  Pearson ............................ 260/310 R Primary Examiner—Donald G. Daus
Assistant Examiner—James H. Turnipseed
Attorney, Agent, or Firm—Millen & White

[57] ABSTRACT

Nitroimidazoles of the formula

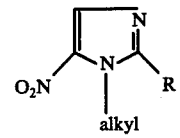

wherein R is dialkylaminoacryloyl; 3-, 4-, or 5-pyrazolyl or a mixture thereof which is unsubstituted or substituted by alkyl or, at the 1-position, by hydroxyalkyl or a nitro ester thereof, acyloxyalkyl, nitro, phenyl or phenyl p-substituted by halo, alkoxy or nitro, or, in the 3- or 5-position or a mixture thereof by nitro; 3- or 5-alkyl-4-isooxazolyl or a mixture thereof; or 4-alkyl-5-pyrimidinyl, unsubstituted or substituted by alkyl, amino, 2-furyl or 5-nitro-2-furyl, and the physiologically acceptable acid addition salts thereof, possess antiprotozoal activity, e.g., against *trichomonas vaginalis* and *Entamoeba histolytica*.

23 Claims, No Drawings

NITROIMIDAZOLE DERIVATIVES AND PROCESS FOR THE PREPARATION THEREOF

BACKGROUND OF THE INVENTION

This invention relates to novel nitroimidazole derivatives and to processes for the preparation thereof.

It is known from the literature (C. Cosar, "Arzneimittelforschung" 16, 23 (1966); French Pat. No. 1,212,028) that metronidazole [5-nitro-2-methyl-1-(2-hydroxyethyl)-imidazole] is effective against Trichomonas vaginalis.

The novel nitroimidazoles of this invention exhibit substantially greater antimicrobial effectiveness, especially against protozoa, such as Trichomonas vaginalis and Entamoeba histoytica.

SUMMARY OF THE INVENTION

In a composition aspect, this invention relates to novel nitroimidazole derivatives of the general Formula I

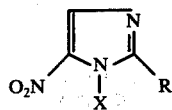

I wherein X is alkyl of 1-4 carbon atoms and R is:

3-dialkylaminoacryloyl of 1-4 carbon atoms in each alkyl group;

3-, 4-, or 5-pyrazolyl, or a mixture thereof, unsubstituted or substituted by one or more of alkyl of 1-4 carbon atoms on a carbon atom, at the 1-position, by alkyl of 1-4 carbon atoms, hydroxyalkyl of 2-5 carbon atoms or a nitric acid ester thereof, acyloxyalkyl of 4-9 carbon atoms, nitro, phenyl or phenyl substituted at the 4-position by a halogen atom, alkoxy of 1-4 carbon atoms or nitro, and at the 3- or 5-position or a mixture thereof, by nitro;

3- or 5-alkyl-4-isoxazolyl or a mixture thereof of 1-4 carbon atoms in the alkyl group; or 4-alkyl-5-pyrimidinyl of 1-4 carbon atoms in the alkyl group, unsubstituted or substituted in the 2-position by alkyl of 1-4 carbon atoms, amino, 2-furyl or 5-nitro-2-furyl; including the physiologically acceptable acid addition salts thereof.

In another composition aspect, this invention relates to compositions comprising a compound of Formula I in admixture with a pharmaceutically acceptable carrier.

In process aspects, this invention relates to processes for the production of compounds of Formula I and their use as antimicrobial agents.

DETAILED DISCUSSION

The compounds of Formula I include those wherein X is preferably methyl and R is (a)

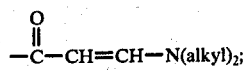

(b)

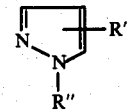

joined at the 3, 4 or 5 carbon atom or mixtures thereof, wherein R' is H, 3- or 5-nitro or alkyl group of 1-4 carbon atoms and R" is H, alkyl, HO-alkyl, O$_2$NO-alkyl and AcO-alkyl wherein the HO-, O$_2$NO and AcO- groups are $\beta$, $\gamma$, or $\omega$ and the alkyl groups preferably contain 2-3 carbon atoms in the chain and Ac is the acyl radical of an organic, preferably hydrocarbon, carboxylic acid, nitro, phenyl or p-Cl, p-Br, p-F, p-alkoxy or p-NO$_2$ phenyl;

(c)

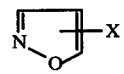

joined at the 3- or 5-carbon atom and wherein X is 3- or 5-alkyl;

(d)

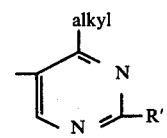

wherein R' is alkyl, NH$_2$, 2-furyl or 5-nitro-2-furyl; including acid addition salts of each of the above which are basic enough to form such salts.

The processes of this invention sometimes produce isomeric mixtures when R is pyrazolyl or isozazolyl. Thus, compounds of groups (b) above can be obtained as mixtures of 3-, 4- and/or 5-pyrazolyl isomers. Similarly, the compounds of group (c) can be obtained as mixtures of 3- and 5-isoxazolyl isomers. These mixtures are useful as antimicrobial agents and the individual compounds in the mixtures need not be isolated therefrom.

Examples of alkyl of 1-4 carbon atoms in the above compounds of Formula I are methyl, ethyl, propyl, n-butyl, isobutyl, or tert.-butyl groups, with methyl preferred.

Examples of hydroxyalkyl of 2-5 carbon atoms are 3-hydroxypropyl, 4-hydroxybutyl, and 5-hydroxypentyl and the preferred 2-hydroxyethyl. In the nitric acid esters thereof, the OH group is replaced by an ONO$_2$ group. Examples of acyloxyalkyl are the esters of the aforementioned hydroxyalkyl groups with hydrocarboncarboxylic, preferably alkanecarboxylic acids of 2-4 carbon atoms, e.g., acetic acid, propionic acid and butyric acid. Contemplated as equivalents of these alkanecarboxylic acid esters are esters of substituted and dibasic carboxylic acids and sulfonic, sulfuric and phosphoric acids, including hydrocarboncarboxylic acids and sulfonic acids of 1-15 carbon atoms of the aliphatic, cycloaliphatic, aromatic, aromatic-aliphatic series, those of the heterocyclic series and those which are unsaturated and/or polybasic and/or substituted in the usual manner, e.g., by alkyl, hydroxy, alkoxy, oxo, or amino groups, or halogen atoms.

Specific examples of such equivalent esters are esters of formic acid and alkanoic acids of more than 4 carbon atoms, e.g., valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert.-butylacetic acid of cycloalkylcarboxylic and cycloalkylalkanoic acids, e.g., cyclopentylacetic acid, cyclohexylacetic acid, cyclohexanecarboxylic acid and of aryl carbocyclic carboxylic and aryl carbocyclicalkanoic acids of 7–15, preferably 7–12, carbon atoms, e.g., benzoic and phenylacetic acid. Other equivalent esters are esters of, e.g., phenoxyacetic acid, mono-, di-, and trichloroacetic acid, aminoacetic acid, dimethylaminoacetic acid, piperidinoacetic acid, morpholinoacetic acid, lactic acid, succinic acid, adipic acid, benzoic acid, nicotinic acid, isonicotinic acid, furan-2-carboxylic acid.

Examples of equivalent esters of sulfonic acids are esters of alkanesulfonic acids of 1-6 carbon atoms, e.g., methanesulfonic acid, ethanesulfonic acid, butanesulfonic acid, cycloalkanesulfonic acids of 3-8 carbon atoms, e.g., cyclopentanesulfonic acid and cyclohexanesulfonic acid, and aryl carbocyclicsulfonic acids of 6-12 carbon atoms, e.g., benzenesulfonic acid and p-toluenesulfonic acid and the corresponding acid bearing one or more substituents, e.g., β-chloroethanesulfonic acid, p-chlorobenzenesulfonic acid, N.N-dimethylaminosulfonic acid, N,N-diethylaminosulfonic acid, N,N-bis(β-chloroethyl)aminosulfonic acid, N.N-diisobutylaminosulfonic acid, N,N-dibutylaminosulfonic acid, pyrrolidino-, piperidino-, piperazino-, N-methylpiperazino-, and morpholinosulfonic acid.

Examples of phenyl substituted in the 4-position are those substituted by a halogen atom, e.g., fluorine or bromine atoms and preferably a chlorine atom, by alkoxy, e.g., ethoxy, propoxy, isopropoxy, and n-butoxy, preferably methoxy; and by nitro.

Suitable acids for forming physiologically acceptable acid addition salts are inorganic acids, such as hydrochloric acid, sulfonic acid, phosphoric acid, or organic acids, such as acetic acid, propionic acid, lactic acid, succinic acid, tartaric acid, citric acid, benzoic acid, salicylic acid, nicotinic acid, and heptagluconic acid.

The compounds of this invention are prepared in accordance with conventional operating methods, the most advantageous synthesis being determined by the desired value for R in the end product.

An advantageous method for the preparation of compounds of Formula I wherein R is 3-dialkylaminoacryloyl of 1-4 carbon atoms in each alkyl group or 3(5)-pyrazolyl optionally substituted in the 1-position by alkyl of 1-4 carbon atoms or a phenyl group, comprises reacting a compound of general Formula IIa

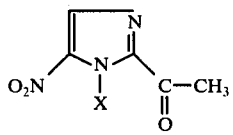

IIa wherein X has the values given above, with a dialkyl formamidoacetal of 1-4 carbon atoms in each alkyl group and thereafter the thus-obtained compounds are condensed with ring closing with hydrazine, an alkyl hydrazine of 1-4 carbon atoms, or a phenylhydrazine.

The reaction of compound IIa with a dialkyl formamidoacetal, preferably the dimethylacetal, is preferably accomplished in a polar aprotic solvent, such as dimethylformamide or dimethyl sulfoxide, at temperatures of from 50° C. to the boiling point of the employed solvent, preferably at temperatures of from 80° C. to the boiling point of the employed solvent.

The thus-obtained dialkylaminoacryloyl nitroimidazoles can be condensed with ring closure with hydrazine or a hydrazine derivative at temperatures of 10°–190° C., preferably at temperatures of from 30° C. to the boiling point of the solvent employed.

Examples of suitable solvents are alcohols, such as methanol and ethanol, dimethylformamide, dimethyl sulfoxide and glycol dimethyl ether.

It is sometimes advantageous to add catalytic amounts of a strong mineral acid, such as hydrochloric acid, to the reaction mixture.

The novel nitroimidazole derivatives of Formula I wherein R is 3(5)-alkyl-4-pyrazolyl, 3(5)-alkyl-4-isoxazolyl, or 4-alkyl-5-pyrimidinyl as defined above are advantageously produced by reacting compounds of the general Formula IIb

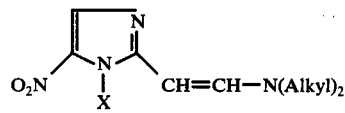

IIb wherein X has the values given above and alkyl is alkyl of 1-4 carbon atoms, with anhydrides or chlorides of alkanecarboxylic acids of 2-5 carbon atoms; and condensing, with ring closure, the thus-obtained compounds of general Formula III

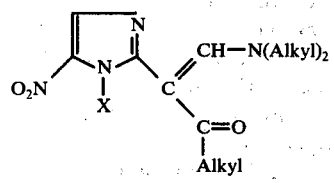

III wherein X and alkyl have the values given above, with a compound of general Formula IV

H₂N — Y    IV wherein Y is amino, alkylamino of 1-4 carbon atoms in the alkyl group, or hydroxyalkylamino of 2-5 carbon atoms in the alkyl group; anilino which can be substituted in the p-position by a halogen atom, alkoxy of 1-4 carbon atoms, or nitro; hydroxy; or

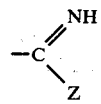

wherein Z is amino, alkyl of 1-4 carbon atoms, furyl or nitrofuryl, or with a salt of one of the above; and optionally thereafter converting a free hydroxy group into a carboxylic acid ester group or transesterifying or saponifying any ester groups present; optionally conventionally nitrating the thus-obtained reaction products; optionally rearranging nitro groups; and optionally converting the thus-obtained reaction products into the salts thereof with physiologically compatible acids.

The compounds of general Formula III are prepared at temperatures of from 10° to 140° C., preferably from 40° C. to the boiling point of the solvent employed, in the absence of a solvent or in a solvent, such as benzene, toluene, acetone, dimethylformamide or tetrahydrofuran.

The compounds of general Formula III are reacted with an amine at temperatures of 10°–190° C., preferably from 30° C. to the boiling point of the solvent used. Suitable solvents are alcohols, such as methanol or ethanol, dimethylformamide, dimethyl sulfoxide, glycol dimethyl ether, etc. If the amine component is used in the form of its salt, a metal alcoholate, such as sodium methylate or sodium ethylate, is preferably added as the acid neutralizing agent.

The esterification of free hydroxy groups takes place in a conventional manner, preferably by reaction with an acid anhydride or an acid chloride.

The transesterification is carried out in a manner known per se, preferably by reaction with another acid, in the presence of a strong mineral acid, e.g., sulfuric acid.

An ester group is saponified in a conventional manner, preferably in an acidic medium. The nitration takes place in a known manner. The nitration in a solvent, such as sulfuric acid, acetic acid, or acetic anhydride is preferred. Nitric acid or potassium nitrate is preferably used as the nitrating agent. The reaction is conducted at temperatures of −10° to 150° C., preferably −10° C. to +30° C.

The rearrangement is effected in a high-boiling solvent, such as benzonitrile, diphenyl oxide, diphenyl, or mixtures of the two last-mentioned solvents, at temperatures of 60° to 280° C., preferably 150° to 280° C.

The novel compounds of general Formula I exhibit good antimicrobial effects, especially against protozoa and, among these, specifically against trichomonads and amebas.

The data in Tables I and II demonstrate the effect of several illustrative compounds against Trichomonas vaginalis and Entamoeba histolytica as compared to metronidazole.

TABLE I

| Compound | Minimum Inhibitory Concentration (MIC) in μg./ml. Against Trich. vag. |
|---|---|
| 3-Dimethylamino-1-(1-methyl-5-nitro-2-imidazolyl)-2-propenone | 0.1 |
| 3-(1-Methyl-5-nitro-2-imidazolyl)-pyrazole | 0.1 |
| 1-Methyl-5-(1-methyl-5-nitro-2-imadazolyl)-pyrazole | 0.05 |
| Metronidazole (in own test) | 1.6 |

TABLE II

| Compound | Minimum Inhibitory Concentration (MIC) in μg./ml. Against | |
|---|---|---|
| | Trich vag. | Entamoeba hist. |
| 3(5)-Methyl-4-(1-methyl-5-nitro-2-imidazolyl)-pyrazole | 0.2 | 12.5 |
| 3-Methyl-4-(1-methyl-5-nitro-2-imidazolyl)-1-nitropyrazole | 0.4 | 25 |
| 1,3-Dimethyl-4-(1-methyl-5-nitro-2-imidazolyl)-pyrazole and 1,5-Dimethyl-4-(1-methyl-5-nitro-2-imidazolyl)-pyrazole in a Ratio of 65 : 35 | 0.1 | 12.5 |
| 2-[5-Methyl-4-(1-methyl-5-nitro-2-imidazolyl)-pyrazolyl]-ethanol | 0.2 | 50 |
| 5-Methyl-4-(1-methyl-5-nitro-2-imidazolyl)-1-phenylpyrazole | 0.1 | 12.5 |
| 1-(4-Chlorophenyl)-5-methyl-4-(1-methyl-5-nitro-2-imidazolyl)-pyrazole | 0.2 | |
| 1-p-Anisyl-5-methyl-4-(1-methyl-5-nitro-2-imidazolyl)-pyrazole | 0.2 | |
| 5-Methyl-4-(1-methyl-5-nitro-2-imidazolyl)-1-(4-nitrophenyl)-pyrazole | 0.4 | |
| 5-Methyl-4-(1-methyl-5-nitro-2-imidazolyl)-isoxazole and 3-Methyl-4-(1-methyl-5-nitro-2-imidazolyl)-isoxazole in a Ratio of 85 : 15 | 0.2 | 50 |
| 4-Methyl-5-(1-methyl-5-nitro-2-imidazolyl)-pyrimidine-2-amine | 0.1 | |
| 2-(2-Furyl)-4-methyl-5-(1-methyl-5-nitro-2-imidazolyl)-pyrimidine | 0.4 | |
| Metronidazole (in own test) | 1.6 | >100 |

The novel compounds can be administered in the usual pharmaceutically acceptable forms of application, such as pills, dragees, capsules, vaginal tablets, elixirs, etc.

Tablets contain, for example, 0.1 – 0.5 g. of active agent, and 0.1 – 5 g. of a pharmacologically inert carrier or adjuvant. Examples of adjuvants for tablets are: lactose, amylose, talc, gelatin and magnesium stearate.

Suitable for topical application are powders, solutions, suspensions, aerosols, and vaginal tablets, and suitable for parenteral application are aqueous and oily solutions or suspensions.

The preparation of the compounds of general Formulae IIa and IIb, utilized as the starting material, is described in German Unexamined Laid-Open Applications DOS Nos. 1,920,150; 1,935,685 and 2,164,412, and U.S. Ser. No. 216,412 filed Dec. 20, 1974, whose disclosures are incorporated by reference. They can be produced by oxidizing the corresponding 1-alkyl-5-nitro-2-(2-dialkylaminovinyl)-imidazoles with ozone or alkali periodate, preferably in the presence of osmium tetroxide catalyst.

Another aspect of this invention are the novel compounds of general Formula III, which are representing valuable intermediates for the preparation of medicinal agents, especially those of general Formula I.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

3-Dimethylamino-1-(1-methyl-5-nitro-2-imidazolyl)-2-propenone 5 g. (30 millimoles) of 5-nitro-1-methyl-2-acetylimidazole and 3.9 g. of dimethylformamide dimethylacetal were maintained in 10 ml. of dimethylformamide at 100° C. for 2 hours. The crystallized product which precipitated during cooling was recrystallized from ethanol.

Yield: 5 g. of 3-dimethylamino-1-(1-methyl-5-nitro-2-imidazolyl)-2-propenone, m.p. 179° C.

EXAMPLE 2

3-(1-Methyl-5-nitro-2-imidazolyl)-pyrazole 0.45 g. (2 millimoles) of 3-dimethylamino-1-(1-methyl-5-nitro-2-imidazolyl)-2-propenone and 0.1 g. of 80% hydrazine hydrate were refluxed in 5 ml. of methanol while adding 2 drops of hydrochloric acid for 3 hours. The crystals precipitated during cooling were recrystallized from ethanol.

Yield: 0.35 g. of 3-(1-methyl-5-nitro-2-imidazolyl)-pyrazole, m.p. 300° C.

EXAMPLE 3

1-Methyl-3-(1-methyl-5-nitro-2-imidazolyl)-pyrazole

This compound was produced analogously to Example 2 with methylhydrazine during a reaction time of 2 hours.

Yield: 0.045 g. of 1-methyl-3-(1-methyl-5-nitro-2-imidazolyl)-pyrazole, m.p. 189° C.

EXAMPLE 4

1-Methyl-5-(1-methyl-5-nitro-2-imidazolyl)-pyrazole

This compound was prepared analogously to Example 2 with methylhydrazine during a reaction time of 5 hours.

Yield: 0.2 g. of 1-methyl-5-(1-methyl-5-nitro-2-imidazolyl)-pyrazole, m.p. 123° C.

EXAMPLE 5

5-(1-Methyl-5-nitro-2-imidazolyl)-1-phenylpyrazole

This substance was produced in analogy to Example 2 with phenylhydrazine in the presence of 3 ml. of hydrochloric acid.

Yield: 0.1 g. of 5-(1-methyl-5-nitro-2-imidazolyl)-1-phenylpyrazole, m.p. 120° C.

EXAMPLE 6

5-Nitro-1-methyl-2-(2-dimethylamino-1-acetylvinyl)-imidazole a. 19.6 g. (0.1 mole) of 2-(2-dimethylaminovinyl)-1-methyl-5-nitroimidazole was refluxed for 3 hours in 250 ml. of acetic anhydride. After concentration, the residue was taken up in acetone, the solution was refluxed with carbon, filtered, and concentrated. This purification process was repeated twice. The crystalline residue was recrystallized from isopropanol.

Yield: 8.2 g. of 5-nitro-1-methyl-2-(2-dimethylamino-1-acetylvinyl)-imidazole, m.p. 129° C.

b. 0.39 g. of 2-(2-dimethylaminovinyl)-1-methyl-5-nitroimidazole in 20 ml. of benzene was refluxed for 3 hours with 160 mg. of acetyl chloride. Concentration to dryness and preparative layer chromatography on silica gel plates yielded 60 mg. of 5-nitro-1-methyl-2-(2-dimethylamino-1-acetylvinyl)-imidazole.

EXAMPLE 7

3(5)-Methyl-4-(1-methyl-5-nitro-2-imidazolyl)-pyrazole 15 g. (0.625 mole) of 5-nitro-1-methyl-2-(2-dimethylamino-1-acetylvinyl)-imidazole and 3.02 g. of hydrazine hydrate were refluxed in 50 ml. of ethanol for 3 hours. After cooling, the crystals were vacuum-filtered.

Yield: 4.4 g. of 3(5)-methyl-4-(1-methyl-5-nitro-2-imidazolyl)-pyrazole, m.p. 191° C.

EXAMPLE 8

3-Methyl-4-(1-methyl-5-nitro-2-imidazolyl)-1-nitropyrazole 0.5 g. (2.4 millimoles) of 3(5)-methyl-4-(1-methyl-5-nitro-2-imidazolyl)-pyrazole was stirred at 20° C. in a mixture of 1.5 ml. of acetic acid and 0.35 ml. of fuming nitric acid for 20 minutes; then, 1 ml. of acetic anhydride was added thereto. After 2 hours of agitation at 20° C., the reaction mixture was poured on ice, neutralized with potassium carbonate, and vacuum-filtered.

Yield: 0.33 g. of 3-methyl-4-(1-methyl-5-nitro-2-imidazolyl)-1-nitropyrazole, m.p. 148° C.

EXAMPLE 9

3-Methyl-4-(1-methyl-5-nitro-2-imidazolyl)-5-nitropyrazole 0.23 g. (0.92 millimole) of 3-methyl-4-(1-methyl-5-nitro-2-imidazolyl)-1-nitropyrazole was refluxed in 3 ml. of benzonitrile for 1 hour. After concentration under vacuum, the mixture was filtered in acetone over a silica gel column. Concentration of the solution and vacuum-filtering yielded 0.05 g. of 3-methyl-4-(1-methyl-5-nitro-2-imidazolyl)-5-nitropyrazole, m.p. 184° C.

EXAMPLE 10

Mixture of 1,3-Dimethyl-4-(1-methyl-5-nitro-2-imidazolyl)-pyrazole and 1,5-Dimethyl-4-(1-methyl-5-nitro-2-imidazolyl)-pyrazole 0.48 g. (0.002 mole) of 5-nitro-1-methyl-2-(2-dimethylamino-1-acetylvinyl)-imidazole was refluxed in 3 ml. of ethanol with 0.2 g. of methylhydrazine for one hour. Cooling and vacuum-filtered yielded 0.2 g. of the mixture of 1,3-dimethyl-4-(1-methyl-5-nitro-2-imidazolyl)-pyrazole and 1,5-dimethyl-4-(1-methyl-5-nitro-2-imidazolyl)-pyrazole in a ratio of 65 : 35 (nuclear resonance spectroscopy); m.p. 118° C.

EXAMPLE 11

2-[5-Methyl-4-(1-methyl-5-nitro-2-imidazolyl)-pyrazolyl]-ethanol 0.48 g. (2 millimoles) of 5-nitro-1-methyl-2-(2-dimethylamino-1-acetylvinyl)-imidazole was refluxed in 5 ml. of ethanol with 0.15 g. of 2-hydrazinoethanol for 3 hours. After concentration, the reaction product was recrystallized from ethanol.

Yield: 0.07 g. of 2-[5-methyl-4-(1-methyl-5-nitro-2-imidazolyl)-pyrazolyl]-ethanol, m.p. 104° C.

EXAMPLE 12

1-(2-Acetoxyethyl)-5-methyl-4-(1-methyl-5-nitro-2-imidazolyl)-pyrazole 2.4 g. (8.2 millimoles) of 2-[5-methyl-4-(1-methyl-5-nitro-2-imidazolyl)-pyrazolyl]-ethanol was left for 1 hour at 100° C. in 20 ml. of acetic anhydride. The mixture was poured on ice and concentrated under vacuum. Recrystallization from cyclohexane/ethanol 2:1 yielded 1.6 g. of 1-(2-acetoxyethyl)-5-methyl-4-(1-methyl-5-nitro-2-imidazolyl)-pyrazole, m.p. 79° C.

EXAMPLE 13

2-[5-Methyl-4-(1-methyl-5-nitro-2-imidazolyl)-pyrazolyl]-ethanol-Nitric Acid Ester 0.6 g. (2 millimoles) of 1-(2-acetoxyethyl)-5-methyl-4-(1-methyl-5-nitro-2-imidazolyl)-pyrazole was agitated for 90 minutes at 50° C. in a mixture of 3 ml. of fuming sulfuric acid and 3 ml. of fuming nitric acid. The mixture was then poured on ice, brought to pH 9 with potassium carbonate, vacuum-filtered, washed with water, and recrystallized from acetonitrile.

Yield: 0.2 g. of 2-[5-methyl-4-(1-methyl-5-nitro-2-imidazolyl)-pyrazolyl]-ethanol-nitric acid ester, m.p. 146° C.

EXAMPLE 14

2-[5-Methyl-4-(1-methyl-5-nitro-2-imidazolyl)-pyrazolyl]-ethanol 0.34 g. (1 millimole) of 1-(2-acetoxyethyl)-5-methyl-4-(1-methyl-5-nitro-2-imidazolyl)-3-nitropyrazole was refluxed in a mixture of 5 ml. of ethanol and 5 ml. of concentrated hydrochloric acid for 3 hours. The reaction mixture was then diluted with 20 ml. of water, neutralized with potassium carbonate, and vacuum-filtered.

Yield: 0.3 g. of 2-[5-methyl-4-(1-methyl-5-nitro-2-imidazolyl)-pyrazolyl]-ethanol.

EXAMPLE 15

5-Methyl-4-(1-methyl-5-nitro-2-imidazolyl)-1-phenyl-pyrazole 0.48 g. (2 millimoles) of 5-nitro-1-methyl-2-(2-dimethylamino-1-acetylvinyl)-imidazole was refluxed for 60 minutes with 0.23 g. of phenylhydrazine in 3 ml. of ethanol. Cooling and vacuum-filtering yielded 0.36 g. of 5-methyl-4-(1-methyl-5-nitro-2-imidazolyl)-1-phenyl-pyrazole, m.p. 194° C.

EXAMPLE 16

1-(4-Chlorophenyl)-5-methyl-4-(1-methyl-5-nitro-2-imidazolyl)-pyrazole 0.48 g. (2 millimoles) of 5-nitro-1-methyl-2-(2-dimethylamino-1-acetylvinyl)-imidazole, 0.35 g. (2 millimoles) of 4-chlorophenylhydrazine hydrochloride, and 1.8 millimoles of sodium ethylate were refluxed in 5 ml. of ethanol for 2 hours. Cooling, vacuum-filtering, and washing with water yielded 0.07 g. of 1-(4-chlorophenyl)-5-methyl-4-(1-methyl-5-nitro-2-imidazolyl)-pyrazole, m.p. 164° C.

EXAMPLE 17

1-p-Anisyl-5-methyl-4-(1-methyl-5-nitro-2-imidazolyl)-pyrazole

This compound was prepared analogously to Example 16 with p-anisylhydrazine hydrochloride.

Yield: 0.25 g. of 1-p-anisyl-5-methyl-4-(1-methyl-5-nitro-2-imidazolyl)-pyrazole, m.p. 165° C.

EXAMPLE 18

5-Methyl-4-(1-methyl-5-nitro-2-imidazolyl)-1-(4-nitrophenyl)-pyrazole

This compound was produced analogously to Example 15 with 4-nitrophenylhydrazine.

Yield: 0.11 g. of 5-methyl-4-(1-methyl-5-nitro-2-imidazolyl)-1-(4-nitrophenyl)-pyrazole, m.p. 210° C.

EXAMPLE 19

Mixture of 5-Methyl-4-(1-methyl-5-nitro-2-imidazolyl)-isoxazole and 3-Methyl-4-(1-methyl-5-nitro-2-imidazolyl)-isoxazole 2.4 g. (0.01 mole) of 5-nitro-1-methyl-2-(2-dimethylamino-1-acetylvinyl)-imidazole and 0.7 g. of hydroxylamine hydrochloride were refluxed for 6 hours in methanol. After cooling, the reaction mixture was concentrated, vacuum-filtered, and recrystallized from ethanol.

Yield: 1.6 g. of the mixture of 5-methyl-4-(1-methyl-5-nitro-2-imidazolyl)-isoxazole and 3-methyl-4-(1-methyl-5-nitro-2-imidazolyl)-isoxazole in a ratio of 85 : 15 (nuclear resonance spectroscopy); m.p. 94° C.

EXAMPLE 20

4-Methyl-5-(1-methyl-5-nitro-2-imidazolyl)-pyrimidine-2-amine 0.96 g. (6 millimoles) of 5-nitro-1-methyl-2-(2-dimethylamino-1-acetylvinyl)-imidazole and 0.76 g. (6 millimoles) of guanidine hydrochloride were refluxed in 5.8 ml. of 1N methanolic sodium methylate solution for 3 hours. After cooling and dilution with 4 ml. of ethanol, the reaction mixture was vacuum-filtered.

Yield: 0.71 g. of 4-methyl-5-(1-methyl-5-nitro-2-imidazolyl)-pyrimidine-2-amine, m.p. 260° C.

EXAMPLE 21

2,4-Dimethyl-5-(1-methyl-5-nitro-2-imidazolyl)-pyrimidine

This compound was prepared analogously to Example 20 with acetamidine hydrochloride.

Yield: 0.27 g. of 2,4-dimethyl-5-(1-methyl-5-nitro-2-imidazolyl)-pyrimidine, m.p. 108° C.

EXAMPLE 22

2-(2-Furyl)-4-methyl-5-(1-methyl-5-nitro-2-imidazolyl)-pyrimidine

This substance was prepared analogously to Example 20 with furan-2-carboxamidine hydrochloride.

Yield: 0.9 g. of 2-(2-furyl)-4-methyl-5-(1-methyl-5-nitro-2-imidazolyl)-pyrimidine, m.p. 151° C.

EXAMPLE 23

4-Methyl-5-(1-methyl-5-nitro-2-imidazolyl)-2-(5-nitro-2-furyl)-pyrimidine a. The compound was prepared analogously to Example 15 with 5-nitrofuran-2-carboxamidine hydrochloride.

Yield: 0.66 g. of 4-methyl-5-(1-methyl-5-nitro-2-imidazolyl)-2-(5-nitro-2-furyl)-pyrimidine, m.p. > 300° C.

b. 0.57 g. (2 millimoles) of 2-(2-furyl)-4-methyl-5-(1-methyl-5-nitro-2-imidazolyl)-pyrimidine in 6 ml. of acetic anhydride was agitated at 0° C. with a mixture of 0.2 ml. of concentrated nitric acid and 0.2 ml. of concentrated sulfuric acid. The mixture was then poured on 10 ml. of ice water and vacuum-filtered.

Yield: 0.18 g. of 4-methyl-5-(1-methyl-5-nitro-2-imidazolyl)-2-(5-nitro-2-furyl)-pyrimidine.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A member of the group consisting of
1. a 5-nitroimidazole of the formula

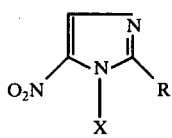

wherein X is alkyl of 1-4 carbon atoms and R is
   a. 3-dialkylamino-acryloyl of 1-4 carbon atoms in each alkyl group;
   b. 3-, 4-, or 5-pyrazolyl which is unsubstituted or which is (i) mono- or di- substituted by alkyl of 1-4 carbon atoms on 1-2 ring carbon atoms, (ii) substituted at the 1-position by alkyl of 1-4 carbon atoms, hydroxyalkyl of 2-5 carbon atoms or a nitric acid ester thereof or a hydrocarbon-carboxylic acid ester thereof of a total of 4-9 carbon atoms, nitro, phenyl or phenyl substituted by a p-halogen atom, p-alkoxy of 1-4 carbon atoms, or p- or m-nitro, or (iii) substituted both on 1-2 ring carbon atoms and at the 1-position as defined hereinabove;
2. a position isomer mixture of pyrazolyl-substituted 5-nitroimidazoles as defined in (1) (b) whose respective pyrazolyl rings are attached at different ring carbon atoms thereof to the 5-nitroimidazole ring; and
3. physiologically acceptable acid addition salts of each of the above.

2. 3-Dimethylamino-1-(1-methyl-5-nitro-2-imidazolyl)-2-propenone, a compound of claim 1.

3. 3-(1-Methyl-5-nitro-2-imidazolyl)-pyrazole, a compound of claim 1.

4. 1-Methyl-3-(1-methyl-5-nitro-2-imidazolyl)-pyrazole, a compound of claim 1.

5. 1-Methyl-5-(1-methyl-5-nitro-2-imidazolyl)-pyrazole, a compound of claim 1.

6. 5-(1-Methyl-5-nitro-2-imidazolyl)-1-phenyl-pyrazole, a compound of claim 1.

7. 3(5)-Methyl-4-(1-methyl-5-nitro-2-imidazolyl)-pyrazole, a compound of claim 1.

8. 3-Methyl-4-(1-methyl-5-nitro-2-imidazolyl)-1-nitropyrazole, a compound of claim 1.

9. 3-Methyl-4-(1-methyl-5-nitro-2-imidazolyl)-5-nitropyrazole, a compound of claim 1.

10. 1,3-Dimethyl-4-(1-methyl-5-nitro-2-imidazolyl)-pyrazole, a compound of claim 1.

11. 1,5-Dimethyl-4-(1-methyl-5-nitro-2-imidazolyl)-pyrazole, a compound of claim 1.

12. 2-[5-Methyl-4-(1-methyl-5-nitro-2-imidazolyl)-pyrazolyl]-ethanol, a compound of claim 1.

13. 1-(2-Acetoxyethyl)-5-methyl-4-(1-methyl-5-nitro-2-imidazolyl)-pyrazole, a compound of claim 1.

14. 2-[5-Methyl-4-(1-methyl-5-nitro-2-imidazolyl)-pyrazolyl]-ethanol-nitric acid ester, a compound of claim 1.

15. 5-Methyl-4-(1-methyl-5-nitro-2-imidazolyl)-1-phenylpyrazole, a compound of claim 1.

16. 1-(4-Chlorophenyl)-5-methyl-4-(1-methyl-5-nitro-2-imidazolyl)-pyrazole, a compound of claim 1.

17. 1-p-Anisyl-5-methyl-4-(1-methyl-5-nitro-2-imidazolyl)-pyrazole, a compound of claim 1.

18. 5-Methyl-4-(1-methyl-5-nitro-2-imidazolyl)-1-(4-nitrophenyl)-pyrazole, a compound of claim 1.

19. A compound of claim 1 wherein R is 3-dialkylaminoacryloyl.

20. A compound of claim 1 wherein R is 3-, 4-, or 5-pyrazolyl which is unsubstituted or which is (i) substituted by alkyl of 1-4 carbon atoms on 1-2 ring carbon atoms, (ii) substituted at the 1-position by alkyl of 1-4 carbon atoms, hydroxyalkyl of 2-5 carbon atoms or a nitric acid ester thereof or a hydrocarboncarboxylic acid ester thereof of a total of 4-9 carbon atoms, nitro, phenyl or phenyl substituted by a p-halogen atom, p-alkoxy of 1-4 carbon atoms, or p- or m-nitro, or (iii) substituted both on 1-2 ring carbon atoms and at the 1-position as defined hereinabove.

21. A position isomer mixture of compounds of claim 1 as defined in (c) thereof.

22. A pharmaceutical composition comprising, in unit dosage form, an anti-protozoal effective amount per unit dosage of a compound of claim 1 or a mixture of position isomers as defined therein, in admixture with a pharmaceutically acceptable carrier.

23. A method of treating protozoal infections which comprises administering systemically or to applying topically to the infected area of a patient with such infection an amount of a compound of claim 1 effective to manifest an anti-protozoal effect.

* * * * *